(12) United States Patent
Burns et al.

(10) Patent No.: US 6,413,239 B1
(45) Date of Patent: Jul. 2, 2002

(54) INFUSION PUMP

(75) Inventors: William H. Burns, Orchard Park, NY (US); John C. McNeirney, Fairburn, GA (US); William S. Gibbons, Jr., Winston-Salem, NC (US)

(73) Assignee: Appro Healthcare, Inc., Buffalo, NY (US)

( * ) Notice: Subject to any disclaimer, the term of this patent is extended or adjusted under 35 U.S.C. 154(b) by 0 days.

(21) Appl. No.: 09/442,014

(22) Filed: Nov. 17, 1999

Related U.S. Application Data
(60) Provisional application No. 60/108,708, filed on Nov. 17, 1998.

(51) Int. Cl.$^7$ .............................................. A61M 37/00
(52) U.S. Cl. .................. 604/132; 222/105; 222/189.06; 222/212
(58) Field of Search .................. 604/131, 132, 604/82, 85, 133, 153; 222/105, 189.06, 386.5, 212

(56) References Cited

U.S. PATENT DOCUMENTS

| | | |
|---|---|---|
| 4,915,693 A | 4/1990 | Hessel |
| 5,080,652 A * | 1/1992 | Sancoff et al. .............. 604/132 |
| 5,167,631 A | 12/1992 | Thompson et al. |
| 5,354,278 A * | 10/1994 | Kriesel |

* cited by examiner

*Primary Examiner*—Brian L. Casler
*Assistant Examiner*—Kevin C. Sirmons
(74) *Attorney, Agent, or Firm*—Phillips, Lytle, Hitchcock, Blaine & Huber LLP

(57) ABSTRACT

The invention is directed to an improved infusion pump (15). In the preferred embodiment, the infusion pump is comprised of an elastomeric hollow balloon (140) and a longitudinal member (110), the balloon having an axial and radial dimension and an open end (22), the longitudinal member (110) having an insertion member (16) extending into the hollow portion (24) of the balloon, the insertion member and the balloon being so configured that the insertion member stretches the elastomeric balloon in the radial direction, but does not stretch the balloon in an axial direction, whereby the infusion pump delivers the quantity of liquid at a substantially constant flow rate. The present invention also discloses an infusion pump comprising a hollow inert membrane (130), an insertion member extending into the hollow portion (23) of the membrane, and the insertion member and the membrane extending into the hollow portion of the balloon, such that the membrane is between the insertion member and the balloon.

1 Claim, 3 Drawing Sheets

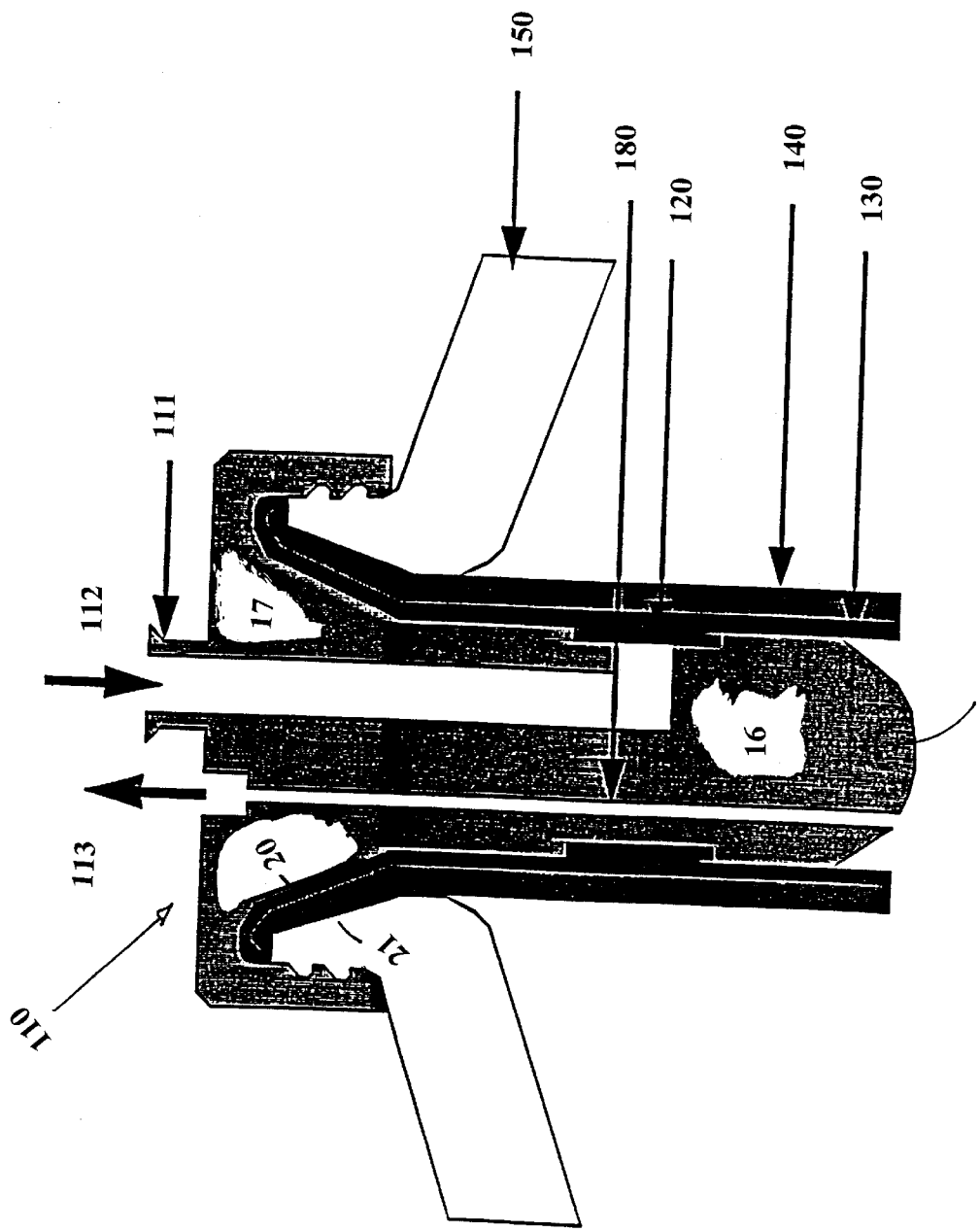

INFUSION PUMP

This application claims benefit of U.S. Provisional appln No. 60/108,708 filed Nov. 17, 1998.

FIELD OF THE INVENTION

The present invention relates generally to the field of infusion pumps and, more particularly, to a disposable, non-gravity fed, elastomeric infusion pump used to infuse fluids intravenously to a patient without dependence on gravity.

BACKGROUND ART

It is often necessary to supply patients intravenously with pharmaceutically active liquids over a long period of time at a controlled rate. It is desirable that this is accomplished while the patient is ambulatory.

Previous devices, such as those described in U.S. Pat. Nos. 5,080,652 and 5,105,983 to Sancoff et al., include elastomeric bladders which, when filled, create pressure to pump the infusor liquid to a patient. These devices, however, are inadequate because they deliver high amounts of fluid at the outset of infusion (40% of fluid in first 25% of time) followed by lower amounts later. Further, these devices result in reduced pressure within the bladder at the terminal end of the infusion cycle, which may result in backflow of infusor liquid into the device from the patient.

U.S. Pat. Nos. 4,915,693 and 4,769,008 to Hessel relate to elastomeric bladder pumps which prestretch the bladder over a stress member both axially and radially, which provides a somewhat more constant pressure profile throughout the cycle. However these devices operate to eliminate the pressure surge within the bladder at the terminal end of the infusion cycle, which may result in backflow of infusor liquid and blood from the patient into the device. Further, prestretching the bladder in both the axial and radial directions requires numerous clamps and other elements, resulting in increased cost and complexity. In addition, because of the need to maintain the chemical integraty of the infusor liquid, these devices are limited in the material which may be used as the bladder. Also, these devices do not include an easy means for sealing the open end of the bladder in a way which does not require clamps and other complicated seals.

The present invention is directed to overcoming these deficiencies.

DISCLOSURE OF THE INVENTION

With parenthetical reference to the corresponding parts, portions or surfaces of the disclosed embodiment, merely for the purposes of illustration and not by way of limitation, the present invention provides an improved infusion pump (15) for delivering a quantity of liquid at a substantially constant flow rate, the infusion pump having an elastomeric hollow balloon (140) and a longitudinal member (110), the balloon having an axial and radial dimension and an open end (22), the longitudinal member having an insertion member (16) extending into the hollow portion (24) of the balloon. The improvement comprises the insertion member and the balloon being so configured that the insertion member stretches the elastomeric balloon in the radial direction, but does not stretch the balloon in an axial direction, whereby the infusion pump delivers the quantity of liquid at a substantially constant flow rate.

The present invention also discloses an infusion pump for delivering a quantity of liquid at a substantially constant flow rate, the pump having an elastomeric hollow balloon and an insertion member, said balloon having an axial and radial dimension and an open end. The improvement comprises a hollow inert membrane (130), the insertion member extending into the hollow portion (23) of the membrane, and the insertion member and the membrane extending into the hollow portion of the balloon, such that the membrane is between the insertion member and the balloon.

The insertion member may comprise an upper portion (18) and a lower portion (19), the upper portion having an upper outside diameter (25) and the lower portion having a lower outside diameter (26), the upper and lower diameters being different. The upper diameter may be greater than the lower diameter. The upper diameter may be about 1.3 to 1.6 times the unstretched inner diameter of the balloon and the lower diameter may be about 1.0 to 1.2 times the unstretched inner diameter of the balloon.

The infusion pump may include a shell. The pump may comprise a shell which includes a bearing surface (21), a longitudinal member which includes a cap section (17), the cap section including a cap bearing surface (20), wherein the cap bearing surface and shell bearing surface are so configured as to seal the open end of the balloon when the shell and the cap section are connected.

Accordingly, the general object of the present invention is to provide a infusion pump which is capable of supplying pharmaceutically active liquids over an extended period of time at a controlled rate.

Another object is to provide an infusion pump with a balloon sealing mechanism which is cost effective and easy to effectuate.

Another object is to provide an infusion pump which protects the chemical and medical integrity of infusor liquids.

Another object is to provide an infusion pump which does not extend axially when in use.

These and other objects and advantages will become apparent from the foregoing and ongoing written specifications, the drawings, and the appended claims.

BRIEF DESCRIPTION OF THE DRAWINGS

FIG. 2 is a longitudinal vertical sectional view of the infusion pump, showing the insert section extending into the balloon.

DESCRIPTION OF THE PREFERRED EMBODIMENTS

Figure 1:
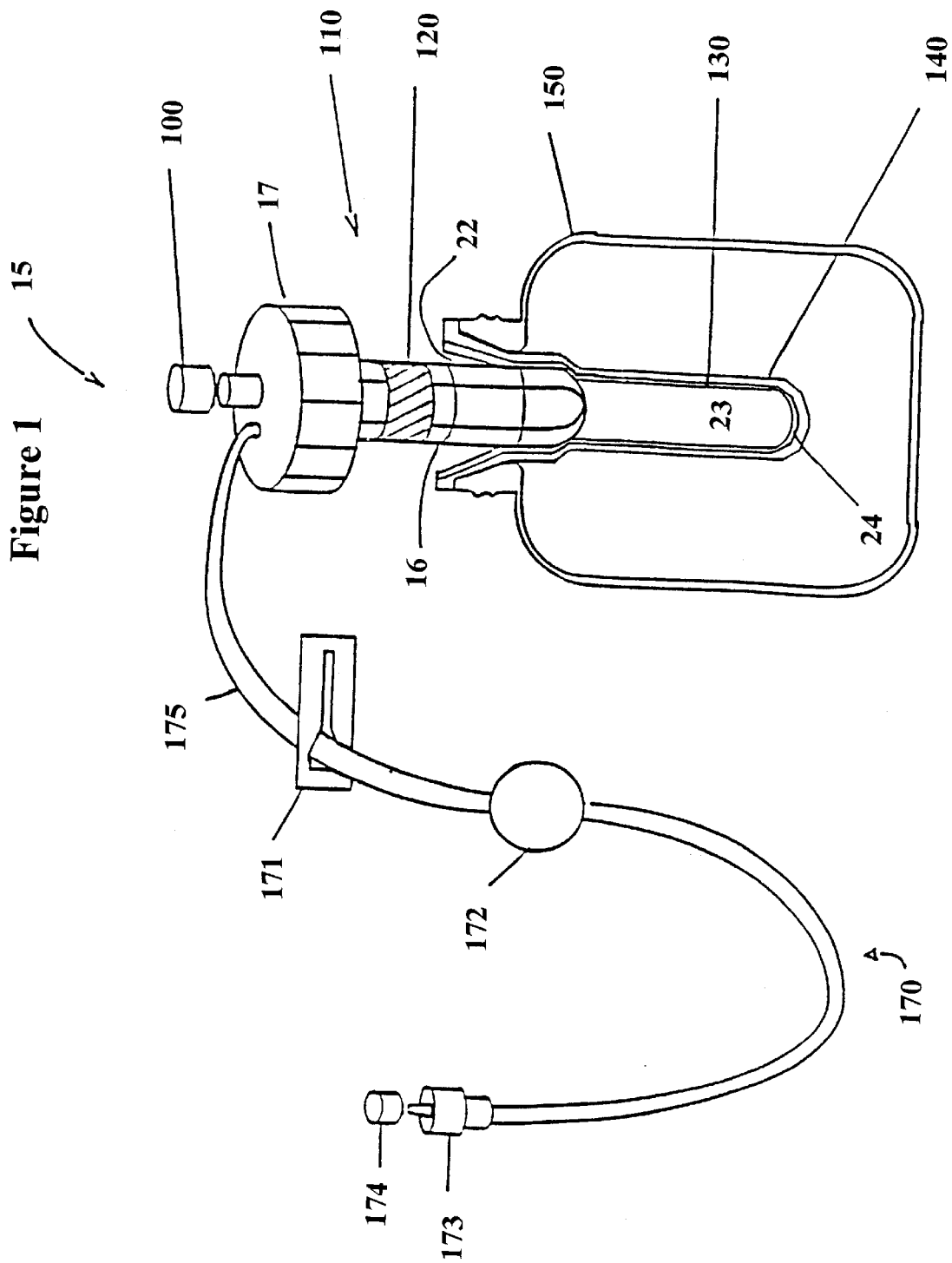
FIG. 1 is a front elevation of the infusion pump, showing the insert section partially extending into the balloon.

At the outset, it should be clearly understood that like reference numerals are intended to identify the same structural elements, portions or surfaces, consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis or elongation, or axis of rotation, as appropriate.

Referring now to the drawings and, more particularly, FIG. 1 thereof, this invention provides an improved disposable device to be used for intravenous infusion of fluids to a patient, of which the presently preferred embodiment is shown at 15. As shown in FIGS. 1–2, the preferred device includes elastomeric balloon 140, longitudinal member 110, which includes an insert section or insertion member 16 and a cap section 17, outlet 180, shell 150, inner membrane 130, and valve 120.

Pump 15 pumps infusor liquid to a patient using pressure created by filling balloon 140. Balloon 140 can be made from any elastomeric material, preferably natural or synthetic rubber. Further, balloon 140 can be any of a variety of elastomeric compositions which will be substantially inert in the presence of the pharmaceutically active material contained in the interior of balloon 140. By inert, it is meant that the material will not adversely react with or dissolve in the pharmaceutically active contents of the filled balloon. Alternatively, as shown in FIGS. 1 and 2, inner membrane 130 may be utilized as a buffer between the infusor liquid and balloon 140. In this preferred embodiment, inner membrane 130 is made of an inert material and balloon 140 is made of any material which has the proper elastomeric properties.

Balloon 140 is initially pre-stretched over insert section 16, such that balloon 140 is initially pressurized, prior to being-filled with infusor liquid. Elastomeric materials typically have an initial region (up to ~10% strain) in which stress changes rapidly relative to imposed strain. Beyond 10% strain, the elastomer maintains relatively constant stress as strain changes. By pre-stretching the elastomer prior to filling, the initial region is avoided and a more constant pressure profile is maintained throughout the filling and emptying of the balloon. Pre-stretching also avoids the delivery of a bolus of fluid at the outset of infusion. Pre-stretching also minimizes the residual volume of the fluid as the balloon empties, because pressure is applied throughout the range of emptying. Further, prestretching balloon 140 in the manner described below prevents backflow from venous pressure during infusion to a patient. Preferably, balloon 140 is prestretched to from about 1.0 to 1.6 times its internal radial diameter when unstretched.

Balloon 140 is not prestretched in its longitudinal or axial direction. That is, the length of insert section 16 is substantially the same as the length of balloon 140. Similarly, inner member 130 is not prestretched in its longitudinal direction as the longitudinal length of member 130 is at least as long as the length of insert section 16.

Figure 5:
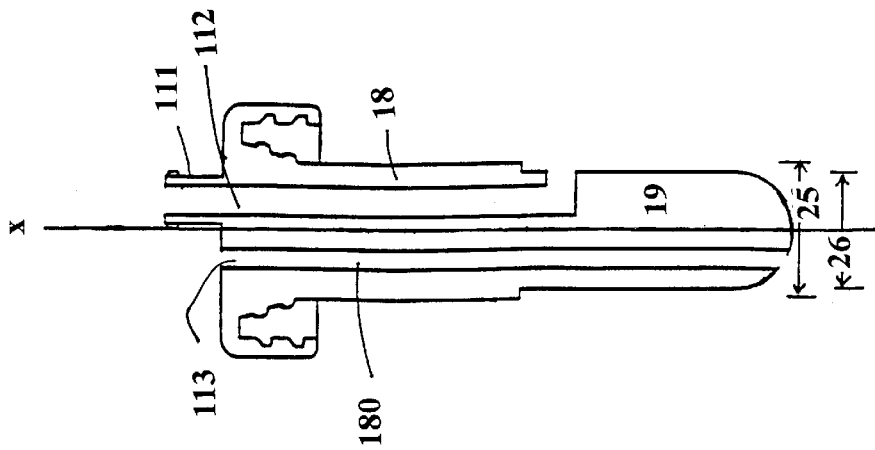
FIG. 5 is a longitudinal vertical sectional view, taken generally on line 5—5 of FIG. 4.
Figure 4:
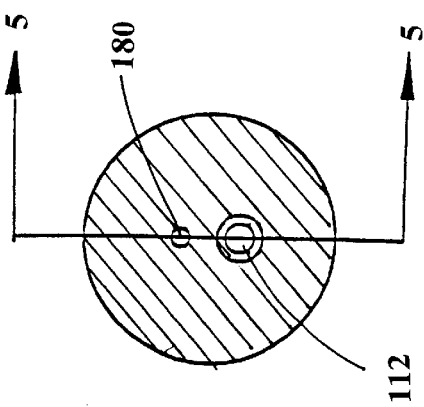
FIG. 4 is a transverse horizontal sectional view, taken generally on line 4—4 of FIG. 3.
Figure 3:
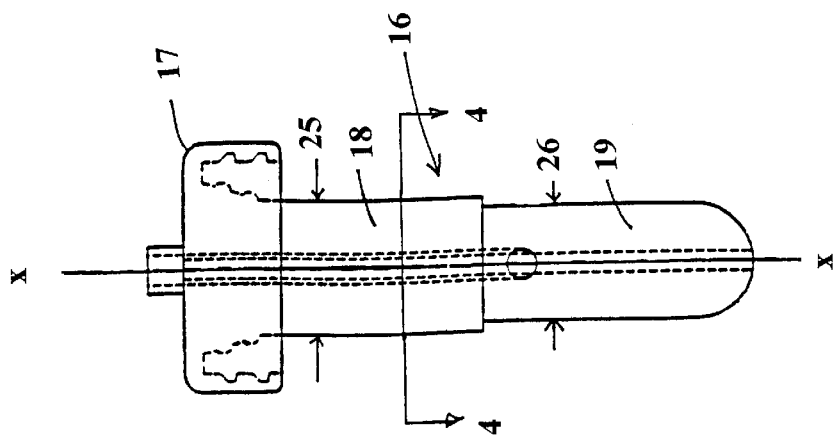
FIG. 3 is a fragmentary view, partly in longitudinal vertical section and partly in right side elevation, showing the longitudinal member of the infusion pump shown in FIG. 2.

As shown in FIGS. 3–5, insert section 16 is a substantially solid cylindrical member elongated along axis x-x. However, as shown in FIG. 3 and 5, the diameter of insert section 16 is not constant. The upper portion 18 has a diameter 25 which is from about 1.3 to 1.6 times the internal unstretched diameter of balloon 140. In the preferred embodiment, the diameter 25 of upper portion 18 of insert member 16 is about 1.4 times the unstretched inner diameter of balloon 140. The lower portion 19 of insert section 16 has a diameter 26 of from about 1.0 to 1.2 times the unstretched inner diameter of balloon 140. In the preferred embodiment, the diameter 26 of lower portion 19 is about 1.05 times the unstretched inner diameter of balloon 140.

By utilizing infusion pump 15, sufficient pressure is maintained in balloon 140 at the terminal end of the infusion cycle that backflow from the patient to the infusion pump due to venous pressure is prevented. As discussed in U.S. Pat. No. 4,915,693 to Hessel and U.S. Pat. No. 4,938,751 to Leeper, which are hereby incorporated by reference, some infusion pumps have been directed to preventing pressure surging at the terminal end of the infusion cycle. In contrast, the infusion pump of the present invention provides a constant flow rate throughout the infusion cycle up to the very end (the terminal end) of the infusion cycle (i.e., the last 3% of cycle time). Prior to the terminal end of the infusion cycle, the infusion pump of the present invention delivers constant flow and has a pressure of from about 5–7 psi. During the terminal end of the cycle, there will be a pressure surge of from about 1–4 psi, preferably from about 2–3 psi, within the infusion pump. This pressure surge has been found to be advantageous, because maintaining a relatively high pressure at the end of the infusion cycle prevents backflow to the infusion pump from the patient due to the patient's venous pressure. Further, the infusion pump of the present invention is less complex and, therefore, less expensive than infusion pumps which attempt to eliminate the pressure surge at the terminal end of the infusion cycle.

Member 110 typically is made of any suitable inert material, such as silicon, Kraton, or PVC, for example.

As shown in FIG. 2, member 110 includes an integrated fill port 112, outlet 180 and exit port 113. Backflow through inlet port 112 is prevented through the use of an elastomeric valve 120. As pressure is applied via fill port 112, the elastomer of elastomeric valve 120 stretches, allowing fluid to flow into inner membrane 130 and fill elastomeric balloon 140. As pressure is released from fill port 112, elastomeric valve 120 contracts and closes fill port 112, preventing backflow. Outlet 180 is a capillary tube, which controls the rate at which fluid exits inner membrane 130 and outer balloon 140. The rate of flow can be controlled for a given infusion device by changing the length and/or the diameter of the exit capillary tube 180. The tube is insert molded into member 110, so that no leaks can occur around capillary tube 180. Alternatively, outlet 180 can comprise other known types of flow control devices. Member 110 may be color coded according to flow rate and/or output volume.

As shown in FIG. 2, member 110 and, in particular, cap section 17 has a frusto-conical upper region 20, which, when bearing against the corresponding frusto-onical surface 21 of shell 150, pinches inner membrane 130 and elastomeric balloon 140 against shell 150. This forms a leak-proof seal through which the contained fluid is prevented from escaping. Member 110 may be attached to shell 150 by a force fit, screw-on, or snap-on connection. Member 110 may be made from a single piece of material which includes insert section 16 and cap section 17, as shown in FIG. 1–3, or may have a separate cap. Shell 150 serves as a protective cover for elastomeric balloon 140, prevents over-filling, and is demarcated to indicate the volume contained in elastomeric balloon 140. In the preferred embodiment, shell 150 is composed of clear polyethylene. Shell 150 may have a region molded for attachment directly to a pole or arm, such as an I.V. pole, gurney, or wheelchair.

In the preferred embodiment, the device uses an ISO standard female luer input port 111, cap 100, and an administration set 170 for output to the infusion site. As shown in FIG. 1, administration set 170 includes tubing 175, in-line, air-venting fluid filter 172, clamp 171, and ISO standard male luer lock 173 and cap 174 at the output site.

The device controls fluid output to within ±10% at a given temperature, throughout the range of infusion. No bolus is infused at the outset of infusion. The device can be used at any height relative to the infusion site, with approximately 5% change in flow rate per foot of head height. For example, infusion from 2 feet below the infusion site results in about 10% slower infusion, and 2 feet above the site increases the infuision rate by about 10%.

The present invention contemplates that many changes and modifications may be made. For example, the particular materials of which the various body parts and component parts are formed are not deemed critical and may be readily varied.

What is claimed is:

1. In an infusion pump for delivering a quantity of liquid at a substantially constant flow rate, said pump having an elastomeric hollow balloon and a longitudinal member, said balloon having an axial and radial dimension and an open end, said longitudinal member having an insertion member extending into the hollow portion of said balloon, the improvement comprising:

said insertion member and said balloon being so configured that said insertion member stretches said elastomeric balloon in a radial direction, but does not stretch said balloon in an axial direction;

a shell;

said shell including a bearing surface;

said longitudinal member including a cap section;

said cap section including a cap bearing surface; and wherein said cap, said cap surface and said shell surface are so configured as to seal said open end of said balloon when said shell and said cap section are connected.

* * * * *